US005689045A

United States Patent [19]
Logemann et al.

[11] Patent Number: 5,689,045
[45] Date of Patent: Nov. 18, 1997

[54] TRANSGENIC PATHOGEN-RESISTANT PLANT

[75] Inventors: Jürgen Logemann, NB Leiden, Netherlands; Guido Jach; Birgit Görnhardt, both of Köln, Germany; John Mundy, V Copenhagen, Denmark; Jeff Schell, Köln; Peter Eckes, Kelkheim, both of Germany; Ilan Chet, Nes Ziona, Israel

[73] Assignee: Max-Planck Gesellschaft zur Forderung Der Wissenschaften, Germany

[21] Appl. No.: 457,797

[22] Filed: Jun. 1, 1995

Related U.S. Application Data

[63] Continuation of Ser. No. 134,416, Oct. 8, 1993, abandoned.

[30] Foreign Application Priority Data

Oct. 9, 1992 [DE] Germany .......................... 42 34 131.0

[51] Int. Cl.⁶ .............. A01H 5/00; C12N 15/29; C12N 15/56; C12N 15/82
[52] U.S. Cl. .................. 800/205; 800/DIG. 17; 800/DIG. 37; 800/DIG. 42; 800/DIG. 43; 800/DIG. 44; 800/DIG. 56; 47/58; 47/DIG. 1; 435/69.1; 435/70.1; 435/172.3; 435/200; 435/209; 435/320.1; 536/23.2; 536/23.6; 536/23.7
[58] Field of Search .................. 800/205, DIG. 17, 800/37, 42–44, 56; 47/58, DIG. 1; 435/69.1, 70.1, 172.3, 200, 209, 320.1; 536/23.2, 23.6, 23.7

[56] References Cited

U.S. PATENT DOCUMENTS 4,940,840 7/1990 Suslow et al. .......................... 800/205
4,970,168 11/1990 Tumer .................................. 435/317.1

FOREIGN PATENT DOCUMENTS

| 8904371 | 5/1989 | European Pat. Off. . |
| 0440304 | 8/1991 | European Pat. Off. ........ C12N 15/56 |
| 9119738 | 12/1991 | European Pat. Off. . |
| 9216632 | 10/1992 | European Pat. Off. . |
| 9217591 | 10/1992 | European Pat. Off. . |
| 9408009 | 4/1994 | European Pat. Off. . |
| 3810286 | 3/1988 | Germany . |
| 4040954 | 12/1990 | Germany . |

OTHER PUBLICATIONS

Potrykus, 1990, Bio/Technology, 8:535–542.
Leah and Mundy, 1989, Plant Molecular Bio., 12:673–682.
Topfer et al., 1987, Nucl. Acids Res., 15:5890.
Hahlbrock and Grisebach, 1979, Ann. Rev. Plant Physiol., 30:105–130.
Dunsmuir et al., "Resistance of *Rhizoctonia Solani* In Transgenic Tobacco", 1993, Curr. Pl. Sci. and BioTech. in Agri. vol. 14, Adv. in Mol. Gen. of Plant–Microbe Interactions, Seattle, Wash., Jul. 1992, Kluwer Acad. Publ., Netherlands, pp. 567–571.
Bojsen et al., "Genetic Transformation of *Nicotiana Benthamiana* with Chitinase and β–1, 3–Glucanase Genes from *Beta Vulgaris* (Sugar Beet)", 1992, Dev. Plant. Pathol. 2 (Mech. of Pl. Def. Res.), Symp. held Aug. 24–27, pp. 449.

(List continued on next page.)

*Primary Examiner*—David T. Fox
*Attorney, Agent, or Firm*—Brumbaugh, Graves, Donohue & Raymond

[57] ABSTRACT

Transgenic pathogen-resistant organism whose genome contains at least two different genes under the control of active promoters with pathogen-inhibiting action. This organism is distinguished by a synergistic pathogen-inhibiting action. This action is evident particularly when the genes code for the gene products chitinase (ChiS, ChiG), glucanase (GluG), protein synthesis inhibitor (PSI) and antifungal protein (AFP).

9 Claims, 2 Drawing Sheets

OTHER PUBLICATIONS

Logemann et al., "Expression of a Barley Ribosome–Inactivating Protein Leads to Increased Fungal Protection in Transgenic Tobacco Plants", 1992, Bio/Technology 10 : 305–308.

Jach et al., "Expression of a Bacterial Chitinase Leads to Improved Resistance of Transgenic Tobacco Plants Against Fungal Infection", 1992, Bio/Technology 1 : 33–40.

Broglie et al., "Transgenic Plants with Enhanced Resistance to the Fungal Pathogen *Rhizoctonia solani*", 1991, Science 254 : 1194–1197.

Wnendt et al. 1990. Nucleic Acids Res. 18(13):3987.

Leah et al. 1991. J. Biol. Chem. 266(3):1564–1573.

Boller, T. 1985. pp. 247–262 In: Cellular And Molec. Biol. Plant Stress, Alan R. Liss, Inc.

Neuhaas et al. 1991. Plant Molec. Biol. 16:141–151.

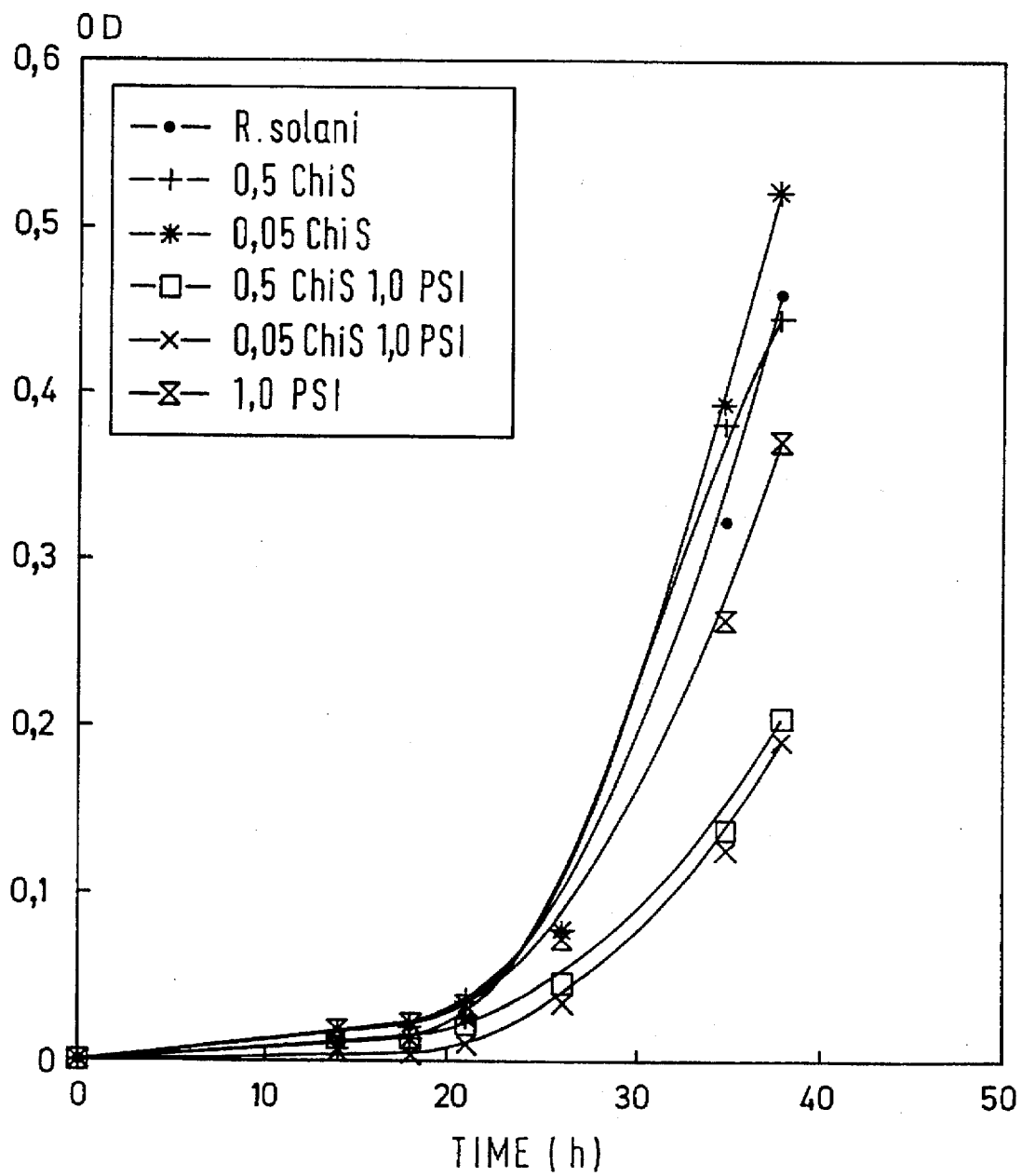

5,689,045

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
( A ) LENGTH: 275 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Aspergillus giganteus ( i x ) FEATURE:
( A ) NAME/KEY: 5'UTR
( B ) LOCATION: 1..45

( i x ) FEATURE:
( A ) NAME/KEY: CDS
( B ) LOCATION: 46..225
( C ) IDENTIFICATION METHOD: experimental
( D ) OTHER INFORMATION: /codon_start=46
/ function="antifungal agent"
/ product="antifungal peptide)"
/ evidence=EXPERIMENTAL
/ note="antifungal agent, especially on
Rhizoctonia solani, various Aspergillus, Fusaria
and Trichophyton species"

( x i ) SEQUENCE DESCRIPTION: SEQ ID NO: 1:

```
TTGCCACCCC CGTTGAAGCC GATTCTCTCA CCGCTGGTGG TCTGG ATG CAA GAG        54
                                                  Met Gln Glu
                                                    1

ATG AGA GCG CGG GTT TTG GCC ACA TAC AAT GGC AAA TGC TAC AAG AAG    102
Met Arg Ala Arg Val Leu Ala Thr Tyr Asn Gly Lys Cys Tyr Lys Lys
      5                   10                  15

GAT AAT ATC TGC AAG TAC AAG GCA CAG AGC GGC AAG ACT GCC ATT TGC    150
Asp Asn Ile Cys Lys Tyr Lys Ala Gln Ser Gly Lys Thr Ala Ile Cys
 20              25                  30                      35

AAG TGC TAT GTC AAA AAG TGC CCC CGC GAC GGC GCG AAA TGC GAG TTT   198
Lys Cys Tyr Val Lys Lys Cys Pro Arg Asp Gly Ala Lys Cys Glu Phe
              40                  45                  50

GAC AGC TAC AAG GGG AAG TGC TAC TGC TAGACGGTGA GCGAAGGGAC          245
Asp Ser Tyr Lys Gly Lys Cys Tyr Cys
              55                  60

GAAGTAGGCT GGGGGTTATT TTACTCTGCT                                   275
```

( 2 ) INFORMATION FOR SEQ ID NO: 2:

( i ) SEQUENCE CHARACTERISTICS:
( A ) LENGTH: 60 amino acids
( B ) TYPE: amino acid
( D ) TOPOLOGY: linear ( i i ) MOLECULE TYPE: protein ( x i ) SEQUENCE DESCRIPTION: SEQ ID NO: 2:

```
Met Gln Glu Met Arg Ala Arg Val Leu Ala Thr Tyr Asn Gly Lys Cys
 1               5                  10                  15

Tyr Lys Lys Asp Asn Ile Cys Lys Tyr Lys Ala Gln Ser Gly Lys Thr
              20                  25                  30

Ala Ile Cys Lys Cys Tyr Val Lys Lys Cys Pro Arg Asp Gly Ala Lys
```

```
                    3 5                           4 0                           4 5
Cys Glu Phe Asp Ser Tyr Lys Gly Lys Cys Tyr Cys
        5 0                       5 5                       6 0
```

( 2 ) INFORMATION FOR SEQ ID NO: 3:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( v ) FRAGMENT TYPE: C-terminal ( v i ) ORIGINAL SOURCE:
        ( A ) ORGANISM: Aspergillus giganteus ( i x ) FEATURE:
        ( A ) NAME/KEY: Protein
        ( B ) LOCATION: 1..51
        ( D ) OTHER INFORMATION: /note="active protein fragment of
            AFP"

( x i ) SEQUENCE DESCRIPTION: SEQ ID NO: 3:

```
Ala Thr Tyr Asn Gly Lys Cys Tyr Lys Lys Asp Asn Ile Cys Lys Tyr
1               5                   1 0                  1 5

Lys Ala Gln Ser Gly Lys Thr Ala Ile Cys Lys Cys Tyr Val Lys Lys
                2 0                  2 5                  3 0

Cys Pro Arg Asp Gly Ala Lys Cys Glu Phe Asp Ser Tyr Lys Gly Lys
            3 5                  4 0                  4 5

Cys Tyr Cys
        5 0
```

( 2 ) INFORMATION FOR SEQ ID NO: 4:

( i ) SEQUENCE CHARACTERISTICS:
        ( A ) LENGTH: 1032 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Hordeum vulgare
        ( B ) STRAIN: L.cv. Piggy ( v i i ) IMMEDIATE SOURCE:
        ( A ) LIBRARY: cDNA gene bank in lambda-gt-11-phages ( i x ) FEATURE:
        ( A ) NAME/KEY: 5'UTR
        ( B ) LOCATION: 1..42

( i x ) FEATURE:
        ( A ) NAME/KEY: CDS
        ( B ) LOCATION: 43..885
        ( D ) OTHER INFORMATION: /codon_start=43
            / function="antifungal activity"
            / product="protein synthesis inhibitor (PSI)"
            / note="antifungal activity, especially on spores
            of Trichoderma reesii and Fusarium sporotrichoides
            and on Rhizoctonia solani."

( i x ) FEATURE:
        ( A ) NAME/KEY: 3'UTR
        ( B ) LOCATION: 886..1032
        ( D ) OTHER INFORMATION: /partial
            / note="46 nucleotides at the 3'-end not shown."

( i x ) FEATURE:
        ( A ) NAME/KEY: polyA_signal (B) LOCATION: 930..935
(D) OTHER INFORMATION: /note="potential polyadenylation signal"

(ix) FEATURE:
(A) NAME/KEY: polyA_signal
(B) LOCATION: 963..976
(D) OTHER INFORMATION: /note="potential polyadenylation signal"

(ix) FEATURE:
(A) NAME/KEY: polyA_signal
(B) LOCATION: 1002..1011
(D) OTHER INFORMATION: /note="potential polyadenylation signal"

(ix) FEATURE:
(A) NAME/KEY: mat_peptide
(B) LOCATION: 46..886

(xi) SEQUENCE DESCRIPTION: SEQ ID NO: 4:

```
CTTAATAGCA CATCTTGTCC GTCTTAGCTT TGCATTACAT CC ATG GCG GCA AAG                    54
                                                Met Ala Ala Lys
                                                 1

ATG GCG AAG AAC GTG GAC AAG CCG CTC TTC ACC GCG ACG TTC AAC GTC                  102
Met Ala Lys Asn Val Asp Lys Pro Leu Phe Thr Ala Thr Phe Asn Val
 5              10                  15                  20

CAG GCC AGC TCC GCC GAC TAC GCC ACC TTC ATC GCC GGC ATC CGC AAC                  150
Gln Ala Ser Ser Ala Asp Tyr Ala Thr Phe Ile Ala Gly Ile Arg Asn
            25                  30                  35

AAG CTC CGC AAC CCG GCG CAC TTC TCC CAC AAC CGC CCC GTG CTG CCG                  198
Lys Leu Arg Asn Pro Ala His Phe Ser His Asn Arg Pro Val Leu Pro
        40                  45                  50

CCG GTC GAG CCC AAC GTC CCG CCG AGC AGG TGG TTC CAC GTC GTG CTC                  246
Pro Val Glu Pro Asn Val Pro Pro Ser Arg Trp Phe His Val Val Leu
    55                  60                  65

AAG GCC TCG CCG ACC AGC GCC GGG CTC ACG CTG GCC ATT CGG GCG GAC                  294
Lys Ala Ser Pro Thr Ser Ala Gly Leu Thr Leu Ala Ile Arg Ala Asp
70                  75                  80

AAC ATC TAC CTG GAG GGC TTC AAG AGC AGC GAC GGC ACC TGG TGG GAG                  342
Asn Ile Tyr Leu Glu Gly Phe Lys Ser Ser Asp Gly Thr Trp Trp Glu
85                  90                  95                 100

CTC ACC CCG GGC CTC ATC CCC GGC GGC ACC TAC GTC GGG TTC GGC GGC                  390
Leu Thr Pro Gly Leu Ile Pro Gly Gly Thr Tyr Val Gly Phe Gly Gly
                105                 110                 115

ACC TAC CGC GAC CTC CTC GGC GAC ACC GAC AAG CTG ACC AAC GTC GCT                  438
Thr Tyr Arg Asp Leu Leu Gly Asp Thr Asp Lys Leu Thr Asn Val Ala
                120                 125                 130

CTC GGC CGG CAG CAG CTC CCG GAC GCG GTG ACC GCC CTC CAC GGG CGC                  486
Leu Gly Arg Gln Gln Leu Pro Asp Ala Val Thr Ala Leu His Gly Arg
            135                 140                 145

ACC AAG GCC GAC AAG CCG TCC GGC CCG AAG CAG CAG CAG GCG AGG GAG                  534
Thr Lys Ala Asp Lys Pro Ser Gly Pro Lys Gln Gln Gln Ala Arg Glu
        150                 155                 160

GCG GTG ACG ACG CTG CTC CTC ATG GTG AAC GAG GCC ACG CGG TTC CAG                  582
Ala Val Thr Thr Leu Leu Leu Met Val Asn Glu Ala Thr Arg Phe Gln
165                 170                 175                 180

ACG GTG TCT GGG TTC GTG GCC GGG TTG CTG CAC CCC AAG GCG GTG GAG                  630
Thr Val Ser Gly Phe Val Ala Gly Leu Leu His Pro Lys Ala Val Glu
                185                 190                 195

AAG AAG AGC GGG AAG ATC GGC AAT GAG ATG AAG GCC CAG GTG AAC GGG                  678
Lys Lys Ser Gly Lys Ile Gly Asn Glu Met Lys Ala Gln Val Asn Gly
                200                 205                 210

TGG CAG GAC CTG TCC GCG GCG CTG CTG AAG ACG GAC GTG AAG CCT CCG                  726
Trp Gln Asp Leu Ser Ala Ala Leu Leu Lys Thr Asp Val Lys Pro Pro
```

-continued

```
                         215                        220                        225
CCG  GGA  AAG  TCG  CCA  GCG  AAG  TTC  GCG  CCG  ATC  GAG  AAG  ATG  GGC  GTG        774
Pro  Gly  Lys  Ser  Pro  Ala  Lys  Phe  Ala  Pro  Ile  Glu  Lys  Met  Gly  Val
     230                      235                       240

AGG  ACG  GCT  GTA  CAG  GCC  GCC  AAC  ACG  CTG  GGG  ATC  CTG  CTG  TTC  GTG        822
Arg  Thr  Ala  Val  Gln  Ala  Ala  Asn  Thr  Leu  Gly  Ile  Leu  Leu  Phe  Val
245                           250                      255                      260

GAG  GTG  CCG  GGT  GGG  TTG  ACG  GTG  GCC  AAG  GCG  CTG  GAG  CTG  TTC  CAT        870
Glu  Val  Pro  Gly  Gly  Leu  Thr  Val  Ala  Lys  Ala  Leu  Glu  Leu  Phe  His
                         265                      270                      275

GCG  AGT  GGT  GGG  AAA  TAGGTAGTTT  TCCAGGTATA  CCTGCATGGG  TAGTGTAAAA             925
Ala  Ser  Gly  Gly  Lys
               280

GTCGAATAAA CATGTCACAG AGTGACGGAC TGATATAAAT AAATAAATAA ACGTGTCACA                   985

GAGTTACATA TAAACAAATA AATAAATAAT TAAAAATGTC CAGTTTA                                 1032
```

(2) INFORMATION FOR SEQ ID NO: 5:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO: 5:

```
Met  Ala  Ala  Lys  Met  Ala  Lys  Asn  Val  Asp  Lys  Pro  Leu  Phe  Thr  Ala
 1                 5                    10                       15

Thr  Phe  Asn  Val  Gln  Ala  Ser  Ser  Ala  Asp  Tyr  Ala  Thr  Phe  Ile  Ala
               20                      25                       30

Gly  Ile  Arg  Asn  Lys  Leu  Arg  Asn  Pro  Ala  His  Phe  Ser  His  Asn  Arg
          35                      40                       45

Pro  Val  Leu  Pro  Pro  Val  Glu  Pro  Asn  Val  Pro  Ser  Arg  Trp  Phe
     50                      55                       60

His  Val  Val  Leu  Lys  Ala  Ser  Pro  Thr  Ser  Ala  Gly  Leu  Thr  Leu  Ala
 65                     70                       75                       80

Ile  Arg  Ala  Asp  Asn  Ile  Tyr  Leu  Glu  Gly  Phe  Lys  Ser  Ser  Asp  Gly
                85                       90                       95

Thr  Trp  Trp  Glu  Leu  Thr  Pro  Gly  Leu  Ile  Pro  Gly  Gly  Thr  Tyr  Val
                100                      105                      110

Gly  Phe  Gly  Gly  Thr  Tyr  Arg  Asp  Leu  Leu  Gly  Asp  Thr  Asp  Lys  Leu
          115                      120                      125

Thr  Asn  Val  Ala  Leu  Gly  Arg  Gln  Gln  Leu  Pro  Asp  Ala  Val  Thr  Ala
     130                      135                      140

Leu  His  Gly  Arg  Thr  Lys  Ala  Asp  Lys  Pro  Ser  Gly  Pro  Lys  Gln  Gln
145                      150                      155                      160

Gln  Ala  Arg  Glu  Ala  Val  Thr  Thr  Leu  Leu  Leu  Met  Val  Asn  Glu  Ala
               165                      170                      175

Thr  Arg  Phe  Gln  Thr  Val  Ser  Gly  Phe  Val  Ala  Gly  Leu  Leu  His  Pro
               180                      185                      190

Lys  Ala  Val  Glu  Lys  Lys  Ser  Gly  Lys  Ile  Gly  Asn  Glu  Met  Lys  Ala
          195                      200                      205

Gln  Val  Asn  Gly  Trp  Gln  Asp  Leu  Ser  Ala  Ala  Leu  Leu  Lys  Thr  Asp
     210                      215                      220

Val  Lys  Pro  Pro  Pro  Gly  Lys  Ser  Pro  Ala  Lys  Phe  Ala  Pro  Ile  Glu
225                      230                      235                      240

Lys  Met  Gly  Val  Arg  Thr  Ala  Val  Gln  Ala  Ala  Asn  Thr  Leu  Gly  Ile
```

```
                          245                         250                         255
Leu  Leu  Phe  Val  Glu  Val  Pro  Gly  Gly  Leu  Thr  Val  Ala  Lys  Ala  Leu
               260                         265                         270

Glu  Leu  Phe  His  Ala  Ser  Gly  Gly  Lys
```

( 2 ) INFORMATION FOR SEQ ID NO: 6:

( i ) SEQUENCE CHARACTERISTICS:
        ( A ) LENGTH: 480 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Hordeum vulgare
        ( B ) STRAIN: L.cv. Piggy ( v i i ) IMMEDIATE SOURCE:
        ( A ) LIBRARY: cDNA gene bank in lambda-gt-11-phages
        ( B ) CLONE: incomplete psi cDNA clone ( i x ) FEATURE:
        ( A ) NAME/KEY: CDS
        ( B ) LOCATION: 1..351
        ( D ) OTHER INFORMATION: /partial
            / codon_start=1
            / function="protein synthesis inhibitor"
            / product="protein synthesis inhibitor"
            / standard_name="PSI"
            / note="aminoterminally incomplete protein from
            an incomplete PSI cDNA clone"

( i x ) FEATURE:
        ( A ) NAME/KEY: 3'UTR
        ( B ) LOCATION: 352..487

( i x ) FEATURE:
        ( A ) NAME/KEY: polyA_signal
        ( B ) LOCATION: 404..409
        ( D ) OTHER INFORMATION: /note="potential polyadenylation
            signal"

( i x ) FEATURE:
        ( A ) NAME/KEY: polyA_signal
        ( B ) LOCATION: 437..442
        ( D ) OTHER INFORMATION: /note="potential polyadenylation
            signal"

( i x ) FEATURE:
        ( A ) NAME/KEY: polyA_signal
        ( B ) LOCATION: 445..450
        ( D ) OTHER INFORMATION: /note="potential polyadenylation
            signal"

( x i ) SEQUENCE DESCRIPTION: SEQ ID NO: 6:

```
GCG  GTG  ACG  ACG  CTG  CTC  CTC  ATG  GTG  AAC  GAG  GCC  ACG  CGG  TTC  CAG      48
Ala  Val  Thr  Thr  Leu  Leu  Leu  Met  Val  Asn  Glu  Ala  Thr  Arg  Phe  Gln
 1                        5                        10                       15

ACG  GTG  TCG  GGG  TTC  GTG  GCC  GGG  CTG  CTG  CAC  CCC  AAG  GCG  GTG  GAG      96
Thr  Val  Ser  Gly  Phe  Val  Ala  Gly  Leu  Leu  His  Pro  Lys  Ala  Val  Glu
               20                       25                       30

AAG  AAG  AGC  GGG  AAG  ATC  GGC  AAT  GAG  ATG  AAG  GCC  CAG  GTG  AAC  GGG     144
Lys  Lys  Ser  Gly  Lys  Ile  Gly  Asn  Glu  Met  Lys  Ala  Gln  Val  Asn  Gly
               35                       40                       45

TGG  CAG  GAC  CTG  TCC  GCG  GCG  CTG  CTG  AAG  ACG  GAC  GTG  AAG  CCC  CCG     192
Trp  Gln  Asp  Leu  Ser  Ala  Ala  Leu  Leu  Lys  Thr  Asp  Val  Lys  Pro  Pro
          50                       55                       60

CCG  GGA  AAG  TCG  CCA  GCG  AAG  TTC  ACG  CCG  ATC  GAG  AAG  ATG  GGC  GTG     240
Pro  Gly  Lys  Ser  Pro  Ala  Lys  Phe  Thr  Pro  Ile  Glu  Lys  Met  Gly  Val
 65                       70                       75                       80
```

-continued

| | | | | | | | | | | | | | | | | |
|---|---|---|---|---|---|---|---|---|---|---|---|---|---|---|---|---|
| AGG | ACT | GCT | GAG | CAG | GCT | GCG | GCT | ACT | TTG | GGG | ATC | CTG | CTG | TTC | GTT | 288 |
| Arg | Thr | Ala | Glu | Gln | Ala | Ala | Ala | Thr | Leu | Gly | Ile | Leu | Leu | Phe | Val | |
| | | | | 85 | | | | | 90 | | | | | 95 | | |
| GAG | GTG | CCG | GGT | GGG | TTG | ACG | GTG | GCC | AAG | GCG | CTG | GAG | CTG | TTT | CAT | 336 |
| Glu | Val | Pro | Gly | Gly | Leu | Thr | Val | Ala | Lys | Ala | Leu | Glu | Leu | Phe | His | |
| | | | 100 | | | | | 105 | | | | | 110 | | | |
| GCG | AGT | GGT | GGG | AAA | TAGGTAGTTT | TGCAGGTATA | CCTGCATGGG | TAAATGTAAA | | | | | | | | 391 |
| Ala | Ser | Gly | Gly | Lys | | | | | | | | | | | | |
| | | | 115 | | | | | | | | | | | | | |

AGTCGAATAA AAATGTCACA GAGTGACGGA CTGATATAAA TAAATTAATA AACATGTCAT    451

CATGAGTGAC AGACTGATAT AAATAAATA    480

( 2 ) INFORMATION FOR SEQ ID NO: 7:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 7:

| Ala | Val | Thr | Thr | Leu | Leu | Leu | Met | Val | Asn | Glu | Ala | Thr | Arg | Phe | Gln |
|---|---|---|---|---|---|---|---|---|---|---|---|---|---|---|---|
| 1 | | | | 5 | | | | | 10 | | | | | 15 | |
| Thr | Val | Ser | Gly | Phe | Val | Ala | Gly | Leu | Leu | His | Pro | Lys | Ala | Val | Glu |
| | | | 20 | | | | | 25 | | | | | 30 | | |
| Lys | Lys | Ser | Gly | Lys | Ile | Gly | Asn | Glu | Met | Lys | Ala | Gln | Val | Asn | Gly |
| | | | 35 | | | | 40 | | | | | 45 | | | |
| Trp | Gln | Asp | Leu | Ser | Ala | Ala | Leu | Leu | Lys | Thr | Asp | Val | Lys | Pro | Pro |
| | 50 | | | | | 55 | | | | | 60 | | | | |
| Pro | Gly | Lys | Ser | Pro | Ala | Lys | Phe | Thr | Pro | Ile | Glu | Lys | Met | Gly | Val |
| 65 | | | | | 70 | | | | 75 | | | | | | 80 |
| Arg | Thr | Ala | Glu | Gln | Ala | Ala | Ala | Thr | Leu | Gly | Ile | Leu | Leu | Phe | Val |
| | | | | 85 | | | | | 90 | | | | | 95 | |
| Glu | Val | Pro | Gly | Gly | Leu | Thr | Val | Ala | Lys | Ala | Leu | Glu | Leu | Phe | His |
| | | | 100 | | | | | 105 | | | | | 110 | | |
| Ala | Ser | Gly | Gly | Lys | | | | | | | | | | | |
| | | | 115 | | | | | | | | | | | | |

( 2 ) INFORMATION FOR SEQ ID NO: 8:

( i ) SEQUENCE CHARACTERISTICS:
        ( A ) LENGTH: 2329 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Serratia marcescens ( v i i ) IMMEDIATE SOURCE:
        ( A ) LIBRARY: Cosmid bank from Serratia marcescens ( i x ) FEATURE:
        ( A ) NAME/KEY: misc_feature
        ( B ) LOCATION: 1..2329
        ( C ) IDENTIFICATION METHOD: experimental
        ( D ) OTHER INFORMATION: /function="exo-chitinase"
            / product="ChiS protein"
            / evidence=EXPERIMENTAL
            / note="sequence listing of the ChiS gene from a
            plasmid pLChiS from E.coli A 5187"

( x i ) SEQUENCE DESCRIPTION: SEQ ID NO: 8:

| | | | | | | |
|---|---|---|---|---|---|---|
| CAGGGCGTTG | TCAATAATGA | CAACACCCTG | GCTGAAGAGT | GTGGTGCAAT | ACTGATAAAT | 60 |
| ATTTATCTTT | CCTTAATAGA | AAATTCACTA | TCCTTATTTG | TCATGTTTTC | TTTTATTTAT | 120 |
| ATGAAAATAA | ATTCACGCTT | GCTGAATAAA | ACCCAGTTGA | TAGCGCTCTT | GTTTTGCGC | 180 |
| CTTTTTTATT | TATAGTACTG | AATGTACGCG | GTGGGAATGA | TTATTTCGCC | ACGTGGAAAG | 240 |
| ACGCTGTTGT | TATTTATTGA | TTTTAACCTT | CGCGGATTAT | TGCGGAATTT | TTTCGCTTCG | 300 |
| GCAATGCATC | GCGACGATTA | ACTCTTTTAT | GTTATCCTC | TCGGAATAAA | GGAATCAGTT | 360 |
| ATGCGCAAAT | TTAATAAACC | GCTGTTGGCG | CTGTTGATCG | GCAGCACGCT | GTGTTCCGCG | 420 |
| GCGCAGGCCG | CCGCGCCGGG | CAAGCCGACC | ATCGCCTGGG | GCAACACCAA | GTTCGCCATC | 480 |
| GTTGAAGTTG | ACCAGGCGGC | TACCGCTTAT | AATAATTTGG | TGAAGGTAAA | AAATGCCGCC | 540 |
| GATGTTTCCG | TCTCCTGGAA | TTTATGGAAT | GGCGACACCG | GCACGACGGC | AAAAGTTTTA | 600 |
| TTAAATGGCA | AAGAGGCGTG | GAGTGGTCCT | TCAACCGGAT | CTTCCGGTAC | GGCGAATTTT | 660 |
| AAAGTGAATA | AAGGCGGCCG | TTATCAAATG | CAGGTGGCAC | TGTGCAATGC | CGACGGCTGC | 720 |
| ACCGCCAGTG | ACGCCACCGA | AATTGTGGTA | GCCGACACCG | ACGGCAGCCA | TTTGGCGCCG | 780 |
| TTGAAAGAGC | CGCTGCTGGA | AAAGAATAAA | CCGTATAAAC | AGAACTCCGG | CAAAGTGGTC | 840 |
| GGTTCTTATT | TCGTCGAGTG | GGGCGTTTAC | GGGCGCAATT | TCACCGTCGA | CAAGATCCCG | 900 |
| GCGCAAAACC | TGACCCACCT | GCTGTACGGC | TTTATCCCGA | TCTGCGGCGG | CAATGGCATC | 960 |
| AACGACAGCC | TGAAAGAGAT | TGAAGGCAGC | TTCCAGGCGT | TGCAGCGCTC | CTGCCAGGGC | 1020 |
| CGCGAGGACT | TCAAAGTCTC | GATCCACGAT | CCGTTCGCCC | GCTGCAAAA | AGCGCAGAAG | 1080 |
| GGCGTGACCG | CCTGGGATGA | CCCCTACAAG | GGCAACTTCG | CCAGCTGAT | GGCGCTGAAG | 1140 |
| CAGGCGCATC | CTGACCTGAA | AATCCTGCCG | TCGATCGGCG | GCTGGACGCT | GTCCGACCCG | 1200 |
| TTCTTCTTCA | TGGGCGACAA | GGTGAAGCGC | GATCGCTTCG | TCGGTTCGGT | GAAAGAGTTC | 1260 |
| CTGCAGACCT | GGAAGTTCTT | CGACGGCGTG | GATATCGACT | GGGAGTTCCC | GGGCGGCAAA | 1320 |
| GGCGCCAACC | CTAACCTGGG | CAGCCCGCAA | GACGGGGAAA | CCTATGTGCT | GCTGATGAAG | 1380 |
| GAGCTGCGGG | CGATGCTGGA | TCAGCTGTCG | GTGGAAACCG | GCCGCAAGTA | TGAGCTGACC | 1440 |
| TCCGCCATCA | GCGCCGGTAA | GGACAAGATC | GACAAGGTGG | CTTACAACGT | TGCGCAGAAC | 1500 |
| TCGATGGATC | ACATCTTCCT | GATGAGCTAC | GACTTCTATG | GCGCCTTCGA | TCTGAAGAAC | 1560 |
| CTGGGGCATC | AGACCGCGCT | GAATGCGCCG | GCCTGGAAAC | CGGACACCGC | CTACACCACG | 1620 |
| GTGAACGGCG | TCAATGCGCT | GCTGGCGCAG | GCGTCAAGC | CGGGCAAAAT | CGTCGTCGGC | 1680 |
| ACCGCCATGT | ATGGCCGCGG | CTGGACCGGG | GTGAACGGCT | ACCAGAACAA | TATTCCGTTC | 1740 |
| ACCGGCACCG | CCACCGGGCC | GGTTAAAGGC | ACCTGGGAGA | ACGGTATCGT | GGACTACCGC | 1800 |
| CAAATCGCCG | GCCAGTTCAT | GAGCGGCGAG | TGGCAGTATA | CCTACGACGC | CACGGCGGAA | 1860 |
| GCGCCTTACG | TGTTCAAACC | TTCCACCGGC | GATCTGATCA | CCTTCGACGA | TGCCCGCTCG | 1920 |
| GTGCAGGCTA | AAGGCAAGTA | CGTGTTGGAT | AAGCAGCTGG | GCGGCCTGTT | CTCCTGGGAG | 1980 |
| ATCGACGCGG | ATAACGGCGA | TATTCTCAAC | AGCATGAACG | CCAGCCTGGG | CAACAGCGCC | 2040 |
| GGCGTTCAAT | AATCGGTTGC | AGTGGTTGCC | GGGGGATATC | CTTTCGCCCC | CGGCTTTTTC | 2100 |
| GCCGACGAAA | GTTTTTTTAC | GCCGCACAGA | TTGTGGCTCT | GCCCCGAGCA | AACGCGCTC | 2160 |
| ATCGGACTCA | CCCTTTTGGG | TAATCCTTCA | GCATTTCCTC | CTGTCTTTAA | CGGCGATCAC | 2220 |
| AAAAATAACC | GTTCAGATAT | TCATCATTCA | GCAACAAAGT | TTTGGCGTTT | TTAACGGAG | 2280 |
| TTAAAAACCA | GTAAGTTTGT | GAGGGTCAGA | CCAATGCGCT | AAAAATGGG | | 2329 |

( 2 ) INFORMATION FOR SEQ ID NO: 9:

( i ) SEQUENCE CHARACTERISTICS:
        ( A ) LENGTH: 1002 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Hordeum vulgare
        ( B ) STRAIN: L.

( i x ) FEATURE:
        ( A ) NAME/KEY: 5'UTR
        ( B ) LOCATION: 1..63

( i x ) FEATURE:
        ( A ) NAME/KEY: CDS
        ( B ) LOCATION: 64..861
        ( D ) OTHER INFORMATION: /codon_start=64
            / function="chitinase"
            / product="26 kD preprotein of chitinase G (ChiG)"
            / note="antifungal activity, especially on
            Trichoderma reesii and Fusarium sporotrichoides as
            well as Rhizoctonia solani and Botrytis cinerea."

( i x ) FEATURE:
        ( A ) NAME/KEY: 3'UTR
        ( B ) LOCATION: 862..1002
        ( D ) OTHER INFORMATION: /partial
            / note="11 nucleotides at 3'end not shown"

( i x ) FEATURE:
        ( A ) NAME/KEY: polyA_signal
        ( B ) LOCATION: 905..910
        ( D ) OTHER INFORMATION: /note="potential polyadenylation
            signal"

( i x ) FEATURE:
        ( A ) NAME/KEY: sig_peptide
        ( B ) LOCATION: 64..294
        ( D ) OTHER INFORMATION: /note="probable signal peptide
            sequence"

( i x ) FEATURE:
        ( A ) NAME/KEY: sig_peptide
        ( B ) LOCATION: 298..312
        ( D ) OTHER INFORMATION: /note="probable signal peptide
            sequence"

( i x ) FEATURE:
        ( A ) NAME/KEY: sig_peptide
        ( B ) LOCATION: 349..378
        ( D ) OTHER INFORMATION: /note="probable signal peptide
            sequence"

( i x ) FEATURE:
        ( A ) NAME/KEY: sig_peptide
        ( B ) LOCATION: 466..588
        ( D ) OTHER INFORMATION: /note="probable signal peptide
            sequence"

( i x ) FEATURE:
        ( A ) NAME/KEY: sig_peptide
        ( B ) LOCATION: 607..861
        ( D ) OTHER INFORMATION: /note="probable signal peptide
            sequence"

( i x ) FEATURE:
        ( A ) NAME/KEY: mat_peptide
        ( B ) LOCATION: 133..861

( x i ) SEQUENCE DESCRIPTION: SEQ ID NO: 9:

```
CCTACGACAG TAGCGTAACG GTAAACACCG AGTACGGTAC TCTGTGCTTT GTTGGCTCGC        60

ACA ATG AGA TCG CTC GCG GTG GTG GTG GCC GTG GTA GCC ACG GTG GCC         108
```

|  | Met<br>-23 | Arg | Ser | Leu<br>-20 | Ala | Val | Val | Val<br>-15 | Ala | Val | Val | Ala | Thr<br>-10 | Val | Ala |  |
|---|---|---|---|---|---|---|---|---|---|---|---|---|---|---|---|---|
| ATG | GCC | ATC | GGC | ACG | GCG | CGC | GGC | AGC | GTG | TCC | TCC | ATC | GTC | TCG | CGC | 156 |
| Met | Ala | Ile | Gly<br>-5 | Thr | Ala | Arg | Gly | Ser<br>1 | Val | Ser | Ser | Ile<br>5 | Val | Ser | Arg |  |
| GCA | CAG | TTT | GAC | CGC | ATG | CTT | CTC | CAC | CGC | AAC | GAC | GGC | GCC | TGC | CAG | 204 |
| Ala | Gln<br>10 | Phe | Asp | Arg | Met | Leu<br>15 | Leu | His | Arg | Asn | Asp<br>20 | Gly | Ala | Cys | Gln |  |
| GCC | AAG | GGC | TTC | TAC | ACC | TAC | GAC | GCC | TTC | GTC | GCC | GCC | GCA | GCC | GCC | 252 |
| Ala | Lys<br>25 | Gly | Phe | Tyr | Thr<br>30 | Tyr | Asp | Ala | Phe | Val<br>35 | Ala | Ala | Ala | Ala | Ala<br>40 |  |
| TTC | CCG | GGC | TTC | GGC | ACC | ACC | GGC | AGC | GCC | GAC | GCC | CAG | AAG | CGC | GAG | 300 |
| Phe | Pro | Gly | Phe | Gly<br>45 | Thr | Thr | Gly | Ser | Ala<br>50 | Asp | Ala | Gln | Lys | Arg<br>55 | Glu |  |
| GTG | GCC | GCC | TTC | CTA | GCA | CAG | ACC | TCC | CAC | GAG | ACC | ACC | GGC | GGG | TGG | 348 |
| Val | Ala | Ala | Phe<br>60 | Leu | Ala | Gln | Thr | Ser<br>65 | His | Glu | Thr | Thr | Gly<br>70 | Gly | Trp |  |
| GCG | ACT | GCA | CCG | GAC | GGG | GCC | TTC | GCC | TGG | GGC | TAC | TGC | TTC | AAG | CAG | 396 |
| Ala | Thr | Ala<br>75 | Pro | Asp | Gly | Ala | Phe<br>80 | Ala | Trp | Gly | Tyr | Cys<br>85 | Phe | Lys | Gln |  |
| GAA | CGT | GGC | GCC | TCC | TCC | GAC | TAC | TGC | ACC | CCG | AGC | GCA | CAA | TGG | CCG | 444 |
| Glu | Arg<br>90 | Gly | Ala | Ser | Ser<br>95 | Asp | Tyr | Cys | Thr | Pro<br>100 | Ser | Ala | Gln | Trp | Pro |  |
| TGC | GCC | CCC | GGG | AAG | CGC | TAC | TAC | GGC | CGC | GGG | CCA | ATC | CAG | CTC | TCC | 492 |
| Cys<br>105 | Ala | Pro | Gly | Lys | Arg<br>110 | Tyr | Tyr | Gly | Arg | Gly<br>115 | Pro | Ile | Gln | Leu | Ser<br>120 |  |
| CAC | AAC | TAC | AAC | TAT | GGA | CCT | GCC | GGC | CGG | GCC | ATC | GGG | GTC | GAT | CTG | 540 |
| His | Asn | Tyr | Asn | Tyr<br>125 | Gly | Pro | Ala | Gly | Arg<br>130 | Ala | Ile | Gly | Val | Asp<br>135 | Leu |  |
| CTG | GCC | AAC | CCG | GAC | CTG | GTG | GCC | ACG | GAC | GCC | ACT | GTG | GGC | TTT | AAG | 588 |
| Leu | Ala | Asn | Pro<br>140 | Asp | Leu | Val | Ala | Thr<br>145 | Asp | Ala | Thr | Val | Gly<br>150 | Phe | Lys |  |
| ACG | GCC | ATC | TGG | TTC | TGG | ATG | ACG | GCG | CAG | CCG | CCC | AAG | CCA | TCG | AGC | 636 |
| Thr | Ala | Ile<br>155 | Trp | Phe | Trp | Met | Thr<br>160 | Ala | Gln | Pro | Pro | Lys<br>165 | Pro | Ser | Ser |  |
| CAT | GCT | GTG | ATC | GCC | GGC | CAG | TGG | AGC | CCG | TCA | GGG | GCT | GAC | CGG | GCC | 684 |
| His | Ala | Val<br>170 | Ile | Ala | Gly | Gln | Trp<br>175 | Ser | Pro | Ser | Gly | Ala<br>180 | Asp | Arg | Ala |  |
| GCA | GGC | CGG | GTG | CCC | GGG | TTT | GGT | GTG | ATC | ACC | AAC | ATC | ATC | AAC | GGC | 732 |
| Ala<br>185 | Gly | Arg | Val | Pro | Gly<br>190 | Phe | Gly | Val | Ile | Thr<br>195 | Asn | Ile | Ile | Asn | Gly<br>200 |  |
| GGG | ATC | GAG | TGC | GGT | CAC | GGG | CAG | GAC | AGC | CGC | GTC | GCC | GAT | CGA | ATC | 780 |
| Gly | Ile | Glu | Cys | Gly<br>205 | His | Gly | Gln | Asp | Ser<br>210 | Arg | Val | Ala | Asp | Arg<br>215 | Ile |  |
| GGG | TTT | TAC | AAG | CGC | TAC | TGT | GAC | ATC | CTC | GGC | GTT | GGC | TAC | GGC | AAC | 828 |
| Gly | Phe | Tyr | Lys<br>220 | Arg | Tyr | Cys | Asp | Ile<br>225 | Leu | Gly | Val | Gly<br>230 | Tyr | Gly | Asn |  |
| AAC | CTC | GAT | TGC | TAC | AGC | CAG | AGA | CCC | TTC | GCC | TAATTAATTA | GTCATGTATT |  |  |  | 881 |
| Asn | Leu | Asp<br>235 | Cys | Tyr | Ser | Gln | Arg<br>240 | Pro | Phe | Ala |  |  |  |  |  |  |
| AATCTTGGCC | CTCCATAAAA | TACAATAAGA | GCATCGTCTC | CTATCTACAT | GCTGTAAGAT |  |  |  |  |  |  |  |  |  |  | 941 |
| GTAACTATGG | TAACCTTTTA | TGGGGAACAT | AACAAAGGCA | TCTCGTATAG | ATGCTTTGCT |  |  |  |  |  |  |  |  |  |  | 1001 |
| A |  |  |  |  |  |  |  |  |  |  |  |  |  |  |  | 1002 |

( 2 ) INFORMATION FOR SEQ ID NO:10:

( i ) SEQUENCE CHARACTERISTICS:
        ( A ) LENGTH: 266 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 10:

| Met<br>-23 | Arg | Ser | Leu<br>-20 | Ala | Val | Val | Ala<br>-15 | Val | Val | Ala | Thr | Val<br>-10 | Ala | Met |
|---|---|---|---|---|---|---|---|---|---|---|---|---|---|---|
| Ala | Ile | Gly<br>-5 | Thr | Ala | Arg | Gly | Ser<br>1 | Val | Ser | Ser<br>5 | Ile | Val | Ser | Arg | Ala |
| Gln<br>10 | Phe | Asp | Arg | Met | Leu<br>15 | Leu | His | Arg | Asn | Asp<br>20 | Gly | Ala | Cys | Gln | Ala<br>25 |
| Lys | Gly | Phe | Tyr | Thr<br>30 | Tyr | Asp | Ala | Phe | Val<br>35 | Ala | Ala | Ala | Ala<br>40 | Phe |
| Pro | Gly | Phe | Gly<br>45 | Thr | Thr | Gly | Ser | Ala<br>50 | Asp | Ala | Gln | Lys | Arg<br>55 | Glu | Val |
| Ala | Ala | Phe<br>60 | Leu | Ala | Gln | Thr | Ser<br>65 | His | Glu | Thr | Thr | Gly<br>70 | Gly | Trp | Ala |
| Thr | Ala<br>75 | Pro | Asp | Gly | Ala | Phe<br>80 | Ala | Trp | Gly | Tyr | Cys<br>85 | Phe | Lys | Gln | Glu |
| Arg<br>90 | Gly | Ala | Ser | Ser | Asp<br>95 | Tyr | Cys | Thr | Pro | Ser<br>100 | Ala | Gln | Trp | Pro | Cys<br>105 |
| Ala | Pro | Gly | Lys | Arg<br>110 | Tyr | Tyr | Gly | Arg | Gly<br>115 | Pro | Ile | Gln | Leu | Ser<br>120 | His |
| Asn | Tyr | Asn | Tyr<br>125 | Gly | Pro | Ala | Gly | Arg<br>130 | Ala | Ile | Gly | Val | Asp<br>135 | Leu | Leu |
| Ala | Asn | Pro<br>140 | Asp | Leu | Val | Ala | Thr<br>145 | Asp | Ala | Thr | Val | Gly<br>150 | Phe | Lys | Thr |
| Ala | Ile<br>155 | Trp | Phe | Trp | Met | Thr<br>160 | Ala | Gln | Pro | Pro | Lys<br>165 | Pro | Ser | Ser | His |
| Ala<br>170 | Val | Ile | Ala | Gly | Gln<br>175 | Trp | Ser | Pro | Ser | Gly<br>180 | Ala | Asp | Arg | Ala | Ala<br>185 |
| Gly | Arg | Val | Pro | Gly<br>190 | Phe | Gly | Val | Ile | Thr<br>195 | Asn | Ile | Ile | Asn | Gly<br>200 | Gly |
| Ile | Glu | Cys | Gly<br>205 | His | Gly | Gln | Asp | Ser<br>210 | Arg | Val | Ala | Asp | Arg<br>215 | Ile | Gly |
| Phe | Tyr | Lys<br>220 | Arg | Tyr | Cys | Asp | Ile<br>225 | Leu | Gly | Val | Gly | Tyr<br>230 | Gly | Asn | Asn |
| Leu | Asp<br>235 | Cys | Tyr | Ser | Gln | Arg<br>240 | Pro | Phe | Ala |

( 2 ) INFORMATION FOR SEQ ID NO:11:

( i ) SEQUENCE CHARACTERISTICS:
        ( A ) LENGTH: 1235 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Hordeum vulgare
        ( B ) STRAIN: L.

( i x ) FEATURE:
        ( A ) NAME/KEY: 5'UTR
        ( B ) LOCATION: 1..48

( i x ) FEATURE:
        ( A ) NAME/KEY: CDS
        ( B ) LOCATION: 49..1050
        ( D ) OTHER INFORMATION: /partial
          / codon_start=49

/ function="glucanase"
/ product="preprotein of the glucanase GluG"

( i x ) FEATURE:
  ( A ) NAME/KEY: 3'UTR
  ( B ) LOCATION: 1051..1235
  ( D ) OTHER INFORMATION: /partial
    / note="14 nucleotides at the 3'end not shown."

( i x ) FEATURE:
  ( A ) NAME/KEY: polyA_signal
  ( B ) LOCATION: 1083..1088
  ( D ) OTHER INFORMATION: /note="potential polyadenylation
    signal"

( i x ) FEATURE:
  ( A ) NAME/KEY: polyA_signal
  ( B ) LOCATION: 1210..1215
  ( D ) OTHER INFORMATION: /note="potential polyadenylation
    signal"

( i x ) FEATURE:
  ( A ) NAME/KEY: mat_peptide
  ( B ) LOCATION: 133..1050

( x i ) SEQUENCE DESCRIPTION: SEQ ID NO: 11:

```
GGCAGCATTG CATAGCATTT GAGCACCAGA TACTCCGTGT GTGCACCA ATG GCT AGA                    57
                                                          Met Ala Arg
                                                          -28

AAA GAT GTT GCC TCC ATG TTT GCA GTT GCT CTC TTC ATT GGA GCA TTC                    105
Lys Asp Val Ala Ser Met Phe Ala Val Ala Leu Phe Ile Gly Ala Phe
-25             -20                 -15                 -10

GCT GCT GTT CCT ACG AGT GTG CAG TCC ATC GGC GTA TGC TAC GGC GTG                    153
Ala Ala Val Pro Thr Ser Val Gln Ser Ile Gly Val Cys Tyr Gly Val
              -5                  1                 5

ATC GGC AAC AAC CTC CCC TCC CGG AGC GAC GTG GTG CAG CTC TAC AGG                    201
Ile Gly Asn Asn Leu Pro Ser Arg Ser Asp Val Val Gln Leu Tyr Arg
            10                  15                  20

TCC AAG GGC ATC AAC GGC ATG CGC ATC TAC TTC GCC GAC GGG CAG GCC                    249
Ser Lys Gly Ile Asn Gly Met Arg Ile Tyr Phe Ala Asp Gly Gln Ala
        25                  30                  35

CTC TCG GCC GTC CGC AAC TCC GGC ATC GGC CTC ATC CTC GAC ATC GGC                    297
Leu Ser Ala Val Arg Asn Ser Gly Ile Gly Leu Ile Leu Asp Ile Gly
40                  45                  50                  55

AAC GAC CAG CTC GCC AAC ATC GCC GCC AGC ACC TCC AAC GCG GCC TCC                    345
Asn Asp Gln Leu Ala Asn Ile Ala Ala Ser Thr Ser Asn Ala Ala Ser
                60                  65                  70

TGG GTC CAG AAC AAC GTG CGG CCC TAC TAC CCT GCC GTG AAC ATC AAG                    393
Trp Val Gln Asn Asn Val Arg Pro Tyr Tyr Pro Ala Val Asn Ile Lys
            75                  80                  85

TAC ATC GCC GCC GGC AAC GAG GTG CAG GGC GGC GCC ACG CAG AGC ATC                    441
Tyr Ile Ala Ala Gly Asn Glu Val Gln Gly Gly Ala Thr Gln Ser Ile
        90                  95                  100

CTG CCG GCC ATG CGC AAC CTC AAC GCG GCC CTC TCC GCG GCG GGG CTC                    489
Leu Pro Ala Met Arg Asn Leu Asn Ala Ala Leu Ser Ala Ala Gly Leu
105                 110                 115

GGC GCC ATC AAG GTG TCC ACC TCC ATC CGG TTC GAC GAG GTG GCC AAC                    537
Gly Ala Ile Lys Val Ser Thr Ser Ile Arg Phe Asp Glu Val Ala Asn
120                 125                 130                 135

TCC TTC CCG CCC TCC GCC GGC GTG TTC AAG AAC GCC TAC ATG ACG GAC                    585
Ser Phe Pro Pro Ser Ala Gly Val Phe Lys Asn Ala Tyr Met Thr Asp
                140                 145                 150

GTG GCC CGG CTC CTG GCG AGC ACC GGC GCG CCG CTG CTC GCC AAC GTC                    633
Val Ala Arg Leu Leu Ala Ser Thr Gly Ala Pro Leu Leu Ala Asn Val
            155                 160                 165

TAC CCC TAC TTC GCG TAC CGT GAC AAC CCC GGG AGC ATC AGC CTG AAC                    681
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Tyr | Pro | Tyr | Phe | Ala | Tyr | Arg | Asp | Asn | Pro | Gly | Ser | Ile | Ser | Leu | Asn |      |
|     |     | 170 |     |     |     | 175 |     |     |     | 180 |     |     |     |     |     |      |
| TAC | GCG | ACG | TTC | CAG | CCG | GGC | ACC | ACC | GTG | CGT | GAC | CAG | AAC | AAC | GGG | 729  |
| Tyr | Ala | Thr | Phe | Gln | Pro | Gly | Thr | Thr | Val | Arg | Asp | Gln | Asn | Asn | Gly |      |
|     | 185 |     |     |     | 190 |     |     |     |     | 195 |     |     |     |     |     |      |
| CTG | ACC | TAC | ACG | TCC | CTG | TTC | GAC | GCG | ATG | GTG | GAC | GCC | GTG | TAC | GCG | 777  |
| Leu | Thr | Tyr | Thr | Ser | Leu | Phe | Asp | Ala | Met | Val | Asp | Ala | Val | Tyr | Ala |      |
| 200 |     |     |     | 205 |     |     |     |     | 210 |     |     |     |     |     | 215 |      |
| GCG | CTG | GAG | AAG | GCC | GGC | GCG | CCG | GCG | GTG | AAG | GTG | GTG | GTG | TCG | GAG | 825  |
| Ala | Leu | Glu | Lys | Ala | Gly | Ala | Pro | Ala | Val | Lys | Val | Val | Val | Ser | Glu |      |
|     |     |     |     | 220 |     |     |     | 225 |     |     |     |     |     | 230 |     |      |
| AGC | GGG | TGG | CCG | TCG | GCG | GGC | GGG | TTT | GCG | GCG | TCG | GCC | GGC | AAT | GCG | 873  |
| Ser | Gly | Trp | Pro | Ser | Ala | Gly | Gly | Phe | Ala | Ala | Ser | Ala | Gly | Asn | Ala |      |
|     |     |     | 235 |     |     |     |     | 240 |     |     |     |     | 245 |     |     |      |
| CGG | ACG | TAC | AAC | CAG | GGG | CTG | ATC | AAC | CAC | GTC | GGC | GGG | GGC | ACG | CCC | 921  |
| Arg | Thr | Tyr | Asn | Gln | Gly | Leu | Ile | Asn | His | Val | Gly | Gly | Gly | Thr | Pro |      |
|     |     |     | 250 |     |     |     |     | 255 |     |     |     | 260 |     |     |     |      |
| AAG | AAG | CGG | GAG | GCG | CTG | GAG | ACG | TAC | ATC | TTC | GCC | ATG | TTC | AAC | GAG | 969  |
| Lys | Lys | Arg | Glu | Ala | Leu | Glu | Thr | Tyr | Ile | Phe | Ala | Met | Phe | Asn | Glu |      |
|     | 265 |     |     |     |     | 270 |     |     |     |     | 275 |     |     |     |     |      |
| AAC | CAG | AAG | ACC | GGG | GAC | GCC | ACG | GAG | AGG | AGC | TTC | GGG | CTC | TTC | AAC | 1017 |
| Asn | Gln | Lys | Thr | Gly | Asp | Ala | Thr | Glu | Arg | Ser | Phe | Gly | Leu | Phe | Asn |      |
| 280 |     |     |     |     | 285 |     |     |     |     | 290 |     |     |     |     | 295 |      |
| CCG | GAC | AAG | TCG | CCG | GCA | TAC | AAC | ATC | CAG | TTC | TAGTACGTGT | | | AGCTACCTAG | | 1070 |
| Pro | Asp | Lys | Ser | Pro | Ala | Tyr | Asn | Ile | Gln | Phe |     |     |     |     |     |      |
|     |     |     | 300 |     |     |     |     | 305 |     |     |     |     |     |     |     |      |

CTCACATACC TAAATAAATA AGCTGCACGT ACGTACGTAA TGCGGCATCC AAGTGTAACG           1130

TAGACACGTA CATTCATCCA TGGAAGAGTG CAACCAAGCA TGCGTTAACT TCCTGGTGAT           1190

GATACATCAT CATGGTATGA ATAAAAGATA TGGAAGATGT TATGA                          1235

(2) INFORMATION FOR SEQ ID NO: 12:

(i) SEQUENCE CHARACTERISTICS:
        (A) LENGTH: 334 amino acids
        (B) TYPE: amino acid
        (D) TOPOLOGY: linear (ii) MOLECULE TYPE: protein (xi) SEQUENCE DESCRIPTION: SEQ ID NO: 12:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ala | Arg | Lys | Asp | Val | Ala | Ser | Met | Phe | Ala | Val | Ala | Leu | Phe | Ile |
| -28 |     |     | -25 |     |     |     |     | -20 |     |     |     |     | -15 |     |     |
| Gly | Ala | Phe | Ala | Ala | Val | Pro | Thr | Ser | Val | Gln | Ser | Ile | Gly | Val | Cys |
|     |     | -10 |     |     |     |     | -5  |     |     |     |     | 1   |     |     |     |
| Tyr | Gly | Val | Ile | Gly | Asn | Asn | Leu | Pro | Ser | Arg | Ser | Asp | Val | Val | Gln |
| 5   |     |     |     | 10  |     |     |     |     | 15  |     |     |     |     |     | 20  |
| Leu | Tyr | Arg | Ser | Lys | Gly | Ile | Asn | Gly | Met | Arg | Ile | Tyr | Phe | Ala | Asp |
|     |     |     |     | 25  |     |     |     |     | 30  |     |     |     |     | 35  |     |
| Gly | Gln | Ala | Leu | Ser | Ala | Val | Arg | Asn | Ser | Gly | Ile | Gly | Leu | Ile | Leu |
|     |     |     |     | 40  |     |     |     | 45  |     |     |     |     | 50  |     |     |
| Asp | Ile | Gly | Asn | Asp | Gln | Leu | Ala | Asn | Ile | Ala | Ala | Ser | Thr | Ser | Asn |
|     |     |     | 55  |     |     |     |     | 60  |     |     |     |     | 65  |     |     |
| Ala | Ala | Ser | Trp | Val | Gln | Asn | Asn | Val | Arg | Pro | Tyr | Tyr | Pro | Ala | Val |
|     | 70  |     |     |     |     | 75  |     |     |     |     | 80  |     |     |     |     |
| Asn | Ile | Lys | Tyr | Ile | Ala | Ala | Gly | Asn | Glu | Val | Gln | Gly | Gly | Ala | Thr |
| 85  |     |     |     |     | 90  |     |     |     |     | 95  |     |     |     |     | 100 |
| Gln | Ser | Ile | Leu | Pro | Ala | Met | Arg | Asn | Leu | Asn | Ala | Ala | Leu | Ser | Ala |
|     |     |     |     | 105 |     |     |     |     | 110 |     |     |     |     | 115 |     |

-continued

| | | | | | | | | | | | | | | |
|---|---|---|---|---|---|---|---|---|---|---|---|---|---|---|
| Ala | Gly | Leu | Gly 120 | Ala | Ile | Lys | Val | Ser 125 | Thr | Ser | Ile | Arg | Phe 130 | Asp | Glu |
| Val | Ala | Asn 135 | Ser | Phe | Pro | Pro | Ser 140 | Ala | Gly | Val | Phe | Lys 145 | Asn | Ala | Tyr |
| Met | Thr 150 | Asp | Val | Ala | Arg | Leu 155 | Leu | Ala | Ser | Thr | Gly 160 | Ala | Pro | Leu | Leu |
| Ala 165 | Asn | Val | Tyr | Pro | Tyr 170 | Phe | Ala | Tyr | Arg | Asp 175 | Asn | Pro | Gly | Ser | Ile 180 |
| Ser | Leu | Asn | Tyr | Ala 185 | Thr | Phe | Gln | Pro | Gly 190 | Thr | Thr | Val | Arg | Asp 195 | Gln |
| Asn | Asn | Gly | Leu 200 | Thr | Tyr | Thr | Ser | Leu 205 | Phe | Asp | Ala | Met | Val 210 | Asp | Ala |
| Val | Tyr | Ala 215 | Ala | Leu | Glu | Lys | Ala 220 | Gly | Ala | Pro | Ala | Val 225 | Lys | Val | Val |
| Val | Ser 230 | Glu | Ser | Gly | Trp | Pro 235 | Ser | Ala | Gly | Gly | Phe 240 | Ala | Ala | Ser | Ala |
| Gly 245 | Asn | Ala | Arg | Thr | Tyr 250 | Asn | Gln | Gly | Leu | Ile 255 | Asn | His | Val | Gly | Gly 260 |
| Gly | Thr | Pro | Lys | Lys 265 | Arg | Glu | Ala | Leu | Glu 270 | Thr | Tyr | Ile | Phe | Ala 275 | Met |
| Phe | Asn | Glu | Asn 280 | Gln | Lys | Thr | Gly | Asp 285 | Ala | Thr | Glu | Arg | Ser 290 | Phe | Gly |
| Leu | Phe | Asn 295 | Pro | Asp | Lys | Ser | Pro 300 | Ala | Tyr | Asn | Ile | Gln 305 | Phe |

TRANSGENIC PATHOGEN-RESISTANT PLANT

This application is a continuation of application Ser. No. 08/134,416, filed on Oct. 8, 1993, now abandoned.

FIELD OF THE INVENTION

The invention relates to a pathogen-resistant organism and to a process for generating it.

BACKGROUND OF THE INVENTION

It is known in the state of the art that infestations of a plant by pathogens are caused a series of different reactions. These include, for example, changes in the cell wall structure, the synthesis of phytoalexins which have antimicrobial activity, the accumulation of so-called PR proteins (pathogenesis-related), protease inhibitors and enzymes with hydrolytic functions (Hahlbrock and Grisebach in Ann. Rev. Plant. Physiol., 30 (1979), 105–130).

Many pathogens (fungi and insects) have chitin as a constituent of their cell wall. By contrast, plants possess no chitin. It has now been demonstrated in some cases that there is enhanced production of chitinases in plants after infestation by pathogens. Chitinases are among the enzymes with hydrolytic functions and they catalyze chitin breakdown. It has now been possible to show that plants acquire an increased resistance to pathogens by the production of chitinases.

It is furthermore known to use a gene from barley plants whose gene product codes for an inhibitor of fungal protein synthesis. The incorporation of a corresponding inhibitor gene in transgenic plants led to improved resistance to fungi.

Finally, it has also been disclosed that the use of a polypeptide from *Aspergillus giganteus* is able to protect, by virtue of its antifungal activity, plants from infestation by fungi.

However, given this state of the art there is a need to provide further transgenic pathogen-resistant organisms. Moreover, the organisms which are particularly desired are those whose resistance is increased overall by comparison with the known organisms or is extended with respect to the number of possible pathogens.

This problem is solved by a transgenic pathogen-resistant organism having the features of the present invention.

The invention is based on the surprising finding that the incorporation of at least two different genes with pathogen-inhibiting action into the genome of an organism assists the latter to resist pathogens to an extent going far beyond an additive effect of each of the genes on its own.

The dependent claims indicate further embodiments of the invention.

The genes can code for gene products which reduce the vitality of fungi. In particular, the genes can be of fungal, bacterial and plant, animal or vital origin. In particular, the gene products have properties which promote resistance to fungi. The gene products are chitinase (ChiS, ChiG), glucanase (GluG), protein synthesis inhibitor (PSI) and antifungal protein (AFP).

The transgenic pathogen-resistant organism can be a plant, and tobacco, potato, strawberry, corn, rape or tomato plants are preferred.

The invention also relates to DNA-transfer vectors with inserted DNA sequences as are indicated in detail in this description.

The invention furthermore relates to a process for the generation of pathogen-resistant organisms as are described herein, wherein at least 1 gene with pathogen-inhibiting action is transferred into the genome of an organism, and the pathogen-resistant organism is obtained
(a) by crossing the organism with another, optionally transgenic, organism which contains at least one other gene with pathogen-inhibiting action, and subsequently selecting, and/or
(b) by transformation of this other gene with pathogen-inhibiting action into the organism. The process can be used with DNA-transfer vectors with inserted DNA sequences corresponding to a gene with pathogen-inhibiting action as described herein.

Finally, the invention relates to a process for the generation of pathogen-resistant organisms, wherein vectors which comprise more than one gene with pathogen-inhibiting action are used for the transformation into the genome of an organism.

The invention also relates to a process for ensuring the resistance of organisms to pathogens, characterized in that the organism used is a transgenic pathogen-resistant organism according to the present invention or an organism whose genome contains at least one gene complying with the definitions used herein, and at least one substance which is not expressed by the organism but corresponds to any other one of the gene products complying with the definitions given in this application is applied to the organism.

It was possible to achieve the synergistic effects very particularly with transgenic pathogen-resistant organisms to which the gene sequences which coded for proteins of the attached sequence listings A to E, or corresponded to the latter, were transferred or transfected.

ChiS:

A DNA fragment which is 1.8 Kb in size, that codes for a chitinase called ChiS (SEQ ID NO: 8) was isolated from the soil bacterium *Serratia marcescens*. In vitro investigations with purified ChiS protein showed that it is able effectively to inhibit the growth of fungi, even in low concentrations. The reason for the inhibition is that the ChiS protein has a chitinase activity which is able to damage the tips of the fungal hyphae. In this way the fungus is unable to grow further and is inhibited.

PSI:

The PSI gene originates from barley and codes for a protein which inhibits protein synthesis by fungi. In vitro tests show that even low concentrations of PSI are sufficient to inhibit various fungi such as, for example, *Rhizoctonia solani*.

AFP:

It is possible for a polypeptide which has antifungal activity to be isolated from the fermentation broth of *Aspergillus giganteus* and to be sequenced. This polypeptide is suitable as antifungal agent, for example as spraying agent and as preservative for industrial products and human and animal foods. It can furthermore be combined with other substances which have pesticidal activity, fertilizers or growth regulators. Inhibitory activities against fungi were detectable inter alia against various Aspergillus, Fusaria, Phytophthora and Trichophyton species.

ChiG and GluG:

Two genes which code, respectively, for a chitinase (ChiG) and glucanase (GluG) can be isolated from certain types of barley. Purified ChiG protein or GluG protein inhibits various phytopathogenic fungi in vitro (inter alia *Rhizoctonia solani*) (see R. Leah et al., Journal of Biological Chemistry, Vol. 266, No. 3 (1991), pages 1564–1573).

SUMMARY OF THE INVENTION

The inventors have now found, completely surprisingly, that an at least binary combination of expression of PSI, AFP, ChiS, ChiG or GluG leads to synergistic effects in respect of the acquired resistance to fungi in transgenic plants. In particular, the effects of the individual substances in the combination are markedly exceeded. These include resistance to the fungus Rhizoctonia solani, Sclerotinia infestation, Botrytis infestation, etc.

Combinations according to the invention are (DNA and/or polypeptides):
(binary combinations)
  ChiS, GluG; ChiS, PSI; ChiS, ChiG; ChiS, AFP; GluG, PSI; GluG, ChiG; GluG, AFP; PSI, ChiG; PSI, AFP;
(ternary combinations)
  ChiS, GluG, PSI; ChiS, GluG, ChiG; ChiS, GluG, AFP; GluG, PSI, ChiG; GluG, PSI, AFP; PSI, ChiG, AFP; ChiG, AFP, GluG
(quaternary combinations)
  ChiS, GluG, PSI, AFP; ChiS, GluG, PSI, ChiG;
(quinary combination)
  ChiS, GluG, PSI, AFP, ChiG The invention furthermore relates to the combined use of the proteins with pathogen-inhibiting action, preferably ChiS, PSI, AFP, ChiG and GluG, against pathogens. Combined use also means in this context that at least a first pathogen-inhibiting substance is expressed by the organism and at least a second substance which has pathogen-inhibiting action is applied to the organism from outside.

The agents according to the invention also include those which contain the abovementioned proteins in at least binary combination. The agents according to the invention can contain other active substances besides the proteins. The other active substances can be pesticides, fertilizers and/or growth regulators, and the agents according to the invention can be prepared in various formulations such as concentrates, emulsions, powders, formulations of carriers, mixtures with other active substances, etc. The ChiS/PSI and AFP/PSI combination is particularly preferred. These proteins can be used particularly effectively to inhibit the growth of Rhizoctonia solani, especially in tobacco crops.

BRIEF DESCRIPTION OF THE DRAWINGS

FIG. 2 shows the effects of ChiS and PSI on Rhizoctonia solani.

DETAILED DESCRIPTION OF THE INVENTION

Figure 1:
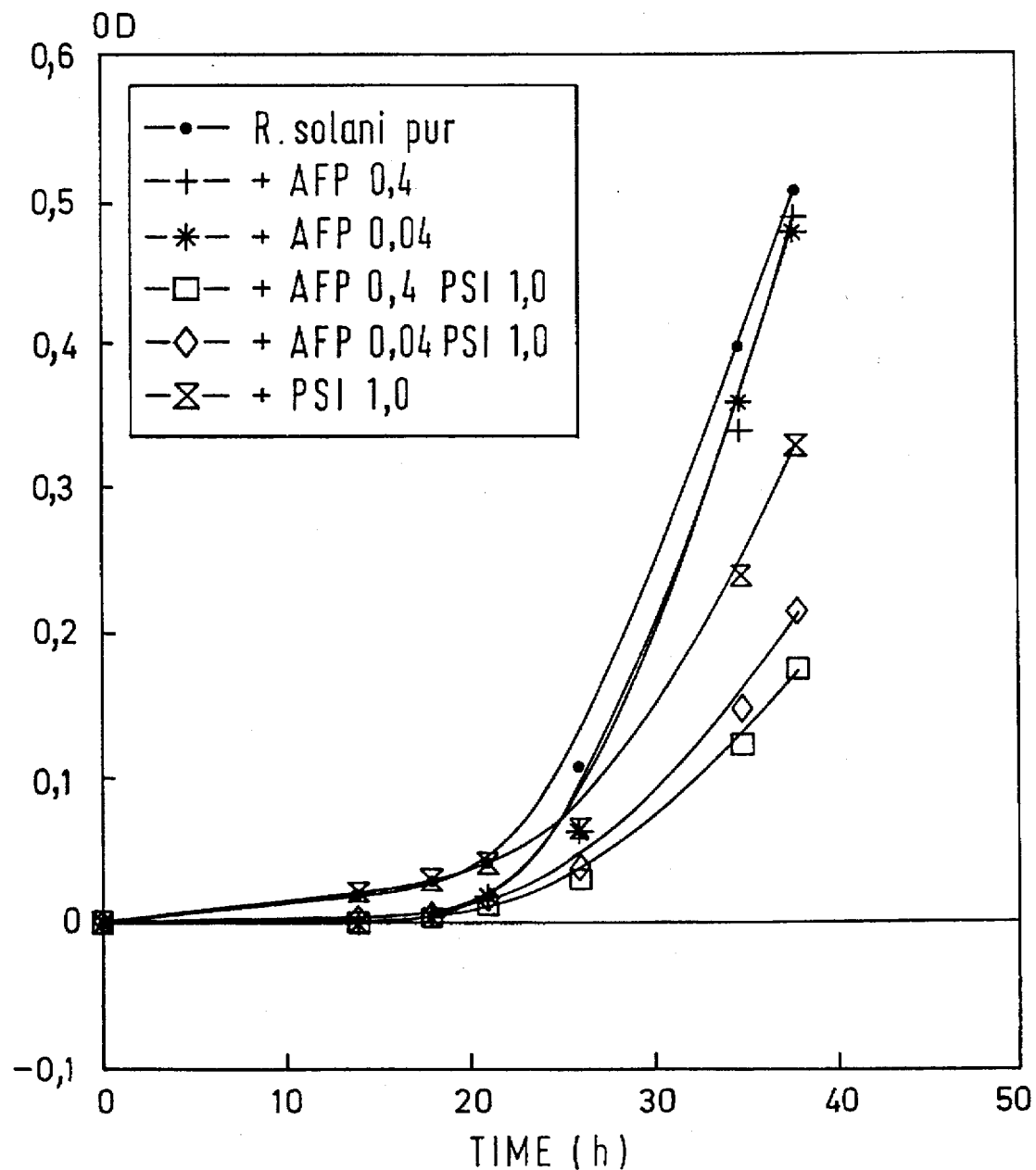
FIG. 1 shows the effects of AFP and PSI on Rhizoctonia solani.

The invention also relates to the use in a process according to the invention of a DNA sequence which codes at least for a polypeptide of sequences A to E, in which sequence A is the sequence of a 60 amino acid AFP protein (SEQ ID NO:2); sequence A' is the sequence of a 51 amino acid AFP protein (SEQ ID NO:3); sequence B is the sequence of the PSI protein (SEQ ID NO:5); sequence B' is the sequence of a protein encoded by an incomplete PSI-cDNA clone (SEQ ID NO:7); sequence D is the sequence of the ChiG protein (SEQ ID NO:10); and sequence E is the sequence of the GluG protein (SEQ ID NO:12) or to a pathogen-resistant organism, where its genome contains at least two different genes under the control of active promoters with pathogen-inhibiting action, where the genes are in each case selected from the group of sequences A to E in which sequence A is the sequence of a nucleic acid (SEQ ID NO:1) which comprises a region encoding AFP protein; sequence B is the sequence of a nucleic acid (SEQ ID NO:4) which comprises a region encoding PSI protein; sequence B' is the sequence of a nucleic acid (SEQ ID NO:6) which was identified as a portion of an incomplete PSI-cDNA clone; sequence C is the sequence of a nucleic acid (SEQ ID NO:8) encoding ChiS protein; sequence D is the sequence of a nucleic acid (SEQ ID NO:9) which comprises a region encoding ChiG protein; and sequence E is the sequence of a nucleic acid (SEQ ID NO:11) which comprises a region encoding GluG protein. The invention furthermore includes DNA sequences which hybridize with a DNA sequence which codes for polypeptides of amino-acid sequences A to E, in which sequence A is the sequence of a 60 amino acid AFP protein (SEQ ID NO:2); sequence A' is the sequence of a 51 amino acid AFP protein (SEQ ID NO:3); sequence B is the sequence of the PSI protein (SEQ ID NO:5); sequence B' is the sequence of a protein encoded by an incomplete PSI-cDNA clone (SEQ ID NO:7); sequence D is the sequence of the ChiG protein (SEQ ID NO:10); and sequence E is the sequence of the GluG protein (SEQ ID NO:12) where these DNA sequences can be of natural, synthetic or semisynthetic origin and can be related to the abovementioned DNA sequence by mutations, nucleotide substitutions, nucleotide deletions, nucleotide insertions and inversions of nucleotide sequences, and for a polypeptide with pathogenic activity. The invention furthermore relates to a recombinant DNA molecule which contains at least one DNA sequence which accords with the preceding statements, where this DNA molecule can be in the form of a cloning or expression vector.

The invention relates to appropriate host organisms and intermediate hosts which are transformed with a recombinant DNA molecule which accords with the preceding statements. Preferred as intermediate host in the generation of a pathogen-resistant transgenic organism are strains of bacteria, in particular so-called Agrobacteria strains.

The invention furthermore relates to the transgenic pathogen-resistant organisms obtained by the process according to the invention, in particular tobacco, potato, corn, pea, rape and tomato plants.

The DNA sequences according to the invention are, as a rule, transferred together with a promoter. Promoter sequences are recognized by the plant transcription apparatus and thus lead to constitutive expression of the gene associated with them in plants. The promoter can, however, also be pathogen-inducible and/or wound-inducible (WUN1) and/or tissue-specific and/or development-specific.

The genetic manipulation operations necessary for carrying out the invention, especially for expression of the gene in plants, are generally known. See for example the publication by Maniatis et al. in "Molecular cloning: A laboratory manual", Cold Spring Harbor (1982).

The invention is explained in detail in the following examples.

All the standard methods of molecular biology were carried out, unless otherwise indicated, as described by Maniatis et al. "Molecular cloning: a laboratory manual", Cold Spring Harbor (1982).

The DNA (SEQ ID NO:1; SEQ ID NO:4; SEQ ID NO:6; SEQ ID NO:8; SEQ ID NO:9; SEQ ID NO:11) coding for amino-acid sequences A to E (SEQ ID NO:2; SEQ ID NO:3; SEQ ID NO:5; SEQ ID NO:7; SEQ ID NO:10; SEQ ID NO:12) was initially cloned in a manner known per se and then transferred by conjugation into A. Tumefaciens LBA 4404 (A. Hoekema et al., Nature 303, 179–180). This took place by the method described by Van Haute et al. in EMBO J. 2, 411–418 (1983).

The transfer of DNA into that Agrobacterium was checked by isolating Agrobacterium DNA by the method described by Ebert et al. in Proc. Natl. Acad. Sci. USA 84 5745–5749 (1987). Restriction cleavage of the DNA, transfer to Hybond-N membrane (Amersham) and hybridization with a radioactively labeled DNA probe provided information about successful DNA transfer into the Agrobacterium.

The transformed Agrobacterium was then used to transform tobaco, rape, strawberry, tomato and potato plants.

The LBA4404 Agrobacteria required for the infection were initially cultivated in selective antibiotic medium (P. Zambryski et al. in EMBO J., 1, 147–152 (1983)), sedimented by centrifugation and washed in YEB medium without antibiotics (YEB=0.5% meat extract; 0.2% yeast extract; 0.5% peptone; 0.5% sucrose; 2 mM $MgSO_4$). After renewed sedimentation and taking up in $MgSO_4$ it was possible to use the bacteria for the infection.

The so-called leaf disk method was used for the infection.

Sterile leaves were used for the leaf disk infection. Leaf pieces about 1 cm in size are dipped in the previously described Agrobacteria suspension and subsequently transferred to 3MS medium (medium described by T. Murashige and F. Skoog in Physiol. Plant., 15, 473–497 (1962); 3MS= MS+3% sucrose). After incubation at 25° C. to 27° C. with 16 hours of light for two days, the leaf pieces were transferred to MSC16 medium (according to T. Murashige (see above); MSC16=MS+0.5 µg/ml BAP +0.1 µg/ml NAA+100 µg/ml kanamycin sulfate +500 µg/ml Claforan). Shoots appearing after 4–6 weeks were cut off and transplanted to MSC15 medium (according to Murashige (see above); MSC15=MS+2% sucrose, 500 µg/ml Claforan +100 µg/ml kanamycin sulfate). Shoots with root formation were analyzed further.

Monocotyledonous plants (including corn), but some dicotyledonous plants too, were transformed by direct gene transfer into protoplasts. These protoplasts were subsequently regenerated to intact plants (Example: J. Potrykus in Biotechnology 8 (1990), 535).

The resulting transgenic plants were infected with the fungus Rhizoctonia solani for testing purposes. For this purpose, fungal cultures were grown and thoroughly mixed in standard soil. This soil was then distributed in a dish and planted with the plants to be tested.

For the evaluation, each plant on a dish was assigned a value from 0 to 3. It was possible to calculate from this for each plant line an index which resulted from the sum of the values. The classification is as follows:

0=no symptoms (healthy)

1=slightly reduced size (compared with a non-infected control); no or very slight visible infestation 2=severe reduction in growth; severe symptoms of infestation 3=dead The rating is carried out in each case 14 days after the start of the series of tests.

EXAMPLE 1

Fungus inhibition test with combined proteins

The intention initially was to show that the proteins used here have synergistic effects in their combination. Fungal growth tests in vitro were carried out for this purpose.

These entailed a defined amount of Rhizoctonia solani fungal mycelium being mixed with 100 µl of potato dextrose solution and incubated in microtiter plates at 25° C. In this test there is a linear correlation between the growth of the fungus and the increase in the optical density at 405 nanometers. The inhibitory effect of proteins can be detected from a smaller increase in the optical density.

2–3 mycelium balls were taken from a liquid culture of R. Solani, mixed with 100 µl of KGB medium in an Eppendorf vessel and carefully homogenized with a glass mortar. This suspension was then mixed with 10 ml of KGB medium and passed through a sterile 100 µm screen. The optical density of this mycelium fragment suspension (100 µl aliquot) was adjusted to a value of 0.06–0.07 at 405 nanometers by adding medium. 100 µl samples were placed on a microtiter plate and mixed with the proteins to be tested. 7 parallels were measured per mixture. Mixtures which were mixed with the corresponding amounts of buffer served as controls. The plates were incubated in the dark at 25° C. for 48 hours, and the optical density of the cultures was measured at regular intervals.

Calculation of whether two proteins act together in an additive synergistic or antagonistic manner in the inhibition of fungal growth is possible from the measured data with the aid of the Colby formula which is described hereinafter and generally used (S. R. Colby in Wheeds, 15 (1967), 20–22).

To do this it was initially necessary to calculate the growth inhibition E to be expected theoretically with an additive behavior (the expected efficacy). This is given by:

$$E = W1 + W2 - ((W1 \times W2)/100)$$

where W1 and W2 indicate the efficacies of the individual proteins, which is defined as that percentage deviation of the growth plot (in the presence of the protein) from the untreated control. The efficacy for a protein (at a defined time in the growth plot) is given by:

$$W1 = (OD(K) - OD(P))/OD(K) \times 100 \text{ (percent)}$$

In this, OD(K) is the optical density of the untreated control and OD(P) is the optical density of the culture treated with the protein.

Thus, on combined use of two proteins, the following statements were possible: if the efficacy G measured in the experiment is identical to the expected value E, the behavior is additive. If, on the other hand, G is greater than E, the behavior is synergistic.

Using this test model, it emerged that the proteins ChiS, PSI, AFP, ChiG and GluG used in the Example surprisingly have synergistic inhibitory effects on various fungi, and these effects were achieved both by the combination of two types of protein and by multiple combination of the above-mentioned proteins.

For example, the following values were determined from the combination of ChiS and PSI protein and from the combination of AFP protein and PSI protein on the fungus Rhizoctonia solani (in each case two different ChiS and AFP concentrations with a constant RIP concentration):

ChiS+PSI:

The expected values were: E1=29.9% and E2=44.5%

The measured values were: G1=60.4% and G2=64.1%

The proteins ChiS and PSI therefore act together in a synergistic manner in the inhibition of the growth of R. Solani.

FIG. 1 shows the results obtained with the combination of the proteins and with the individual substances. According to the Figure, various ChiS concentrations (0.5 µg/ml and 0.05 µg/ml) are combined with PSi protein (1.0 µg/ml).

AFP+PSI:
The expected values were: E1=39.9% and E2=41.9%
The measured values were: G1=57.7% and G2=65.4%
The AFP and PSI combination also according to this shows a synergistic inhibition of growth of the fungus R. Solani. FIG. 2 indicates the test results with various AFP concentrations (0.4 µg/ml and 0.04 µg/ml) combined with PSI protein (1.0 µg/ml).

EXAMPLE 2

Transgenic plants

In order to obtain the organisms according to the invention with DNA sequences which act together synergistically, initially transgenic plants which contained at least one of the genes which act together synergistically were generated.

ChiS in transgenic plants

Initially a ChiS gene was fused to plant regulatory sequences.

A ChiS gene 1.8 Kb in size was sequenced by using synthetic oligonucleotides in the dideoxy sequencing method of Sanger et al. in Proc. Natl. Acad. Sci. USA, 74 (1977), 5463–5467.

The 35S promoter originating from cauliflower mosaic virus (CamV) (400 bp (according to Töpfer et al. in Nucl. Acid. Res., 15 (1987), 5890)) underwent transcriptional fusion to the ChiS gene. The termination signal, which is 0.2 Kb in size, of the 35S gene of CamV, whose functionality in dicotyledonous plants is known, was used 3' from the ChiS gene. The chimeric gene 35S-ChiS was cloned into the pLS034 vector by means of the Agrobacterium tumefaciens transformation system in tobacco and potato plants, and kanamycin-resistant plants were regenerated.

It was possible to detect both the ChiS gene and the corresponding mRNA as well as the gene product protein in the resulting plants.

PSI in transgenic plants

PolyA$^+$ RNA was initially isolated from ripe barley seeds (*Hordeum vulgare* L. cv. Piggy) and deposited in a cDNA gene bank in λ-gt-11-phages. The details of the process are to be found in R. Leah in Plant. Biol., 12 (1989), 673–682. Monospecific PSI antibodies were then used to identify cDNA clones.

Subsequently, the PSI-positive λ-gt-11-phages were isolated, cloned further and sequenced by the dideoxy sequencing method of Sanger et al. indicated above. The DNA cloned into *E. coli* was then transferred in the manner described above by conjugation into Agrobacterium LBA4404.

Both the transferred gene and mRNA and gene product were detectable in corresponding transgenic tobacco, potato, rape, strawberry and tomato plants.

AFP in transgenic plants

For the cloning in the vector, the cDNA sequence of the antifungal peptide is provided with ends which can be ligated into BamH1 and Sal1 restriction cleavage sites. The cloning vector used was pDH51 (Pietrzak et al. in Nucl. Acids Res. 14 (1986), 5857). The vector pDH51 was opened with the restriction enzymes BamH1 and Sal1 between promoter and terminator. The vector pDH51 is a pUC18 derivative which contains promoter and terminator sequences of the 35S transcript from cauliflower mosaic virus. These sequences are recognized by the plant's transcription apparatus and lead to strong constitutive expression of the gene associated with them in plants. The DNA of the antifungal peptide is then cloned via the BamH1 and Sal1 cleavage site into the vector. Finally, the transcription unit—promoter, gene and terminator—is cut out of the vector using the restriction enzyme EcoRI and cloned into a plant transformation vector. The following vectors and their derivatives can, for example, be used as plant transformation vector:

pOCA18 (Olszewski et al. in Nucl. Acids Res., 16 (1988), 10765) pPCV310 (Koncz and Shell in MGG 204 (1986), 383) and pBin19 (Bevan et al. Nucl. Acids. Res. 12 (1984), 8711)

After the transcription unit and the vector had been ligated via the EcoRI cleavage site, the construct was conjugated into the Agrobacterium strain MP90RK (Koncz and Shell (see above)) or IHA101 (Hood et al. in J. Bacteriol. 168 (1986), 1291).

Transgenic tobacco, potato, strawberry, rape and tomato plants were then transformed by the method described above. Transformed shoots are selected on the basis of the cotransferred resistance to the antibiotic kanamycin. Expression of the antifungal protein in the transformed crop plants was checked and confirmed by DNA analysis (Southern blotting), RNA analysis (Northern blotting) and protein analysis with specific antibodies (Western blotting).

ChiG and GluG in transgenic plants

ChiG- and GluG-transgenic plants which were both Southern-, Northern- and Western-positive were obtainable in analogy to the plants described above.

ChiS, PSI, AFP, ChiG, GluG in transgenic monocotyledonous plants

It was possible by means of direct gene transfer to integrate the abovementioned genes into the genome of monocotyledonous plants such as, for example, corn. This resulted in transgenic plants which were Southern- and Northern- and Western-positive.

Combination of various fungus-resistance genes in transgenic plants

The previously obtained tobacco, corn, rape, strawberry, potato and tomato plants were crossed together and selected for plants containing in each case the fungus-resistant genes of both parents. In addition, transgenic plants were obtained by transforming them initially with one and then with one or more other gene. Finally, plants were also transformed with vectors which contained various resistance genes. Fungus-resistance tests were done with this plant material. Surprisingly, in all cases synergistic effects, not just additive effects, in respect of fungus resistance are observed.

For example, a tobacco plant which expresses ChiS and PSI shows a considerably greater resistance to Rhizoctonia infestation than the plants which expressed only ChiS or PSI or which would result from the additive resistance.

A synergistic inhibitory effect on infestation with *Rhizoctonia solani* also results from combined expression of PSI- and AFP-transgenic tobacco. Combination of two or more different genes (ChiS, RIP, AFP, ChiG and GluG) in a wide variety of transgenic plants also led to synergistic inhibitory effects on various fungi.

Whereas wild-type plants have index values from 38 to 46 in tests on 20 seedlings, it emerges with transgenic tobacco according to the invention that the latter grows as well in the presence of the fungus *Rhizoctonia solani* as do control plants (index value 10–12) cultivated on Rhizoctonia-free soil.

We claim:

1. A transgenic plant comprising
   (a) at least one gene, operably linked to a plant-functional promoter, said gene being selected from the group consisting of a ChiG gene from barley having a sequence as set forth in SEQUENCE ID NO. 9, a GluG gene from barley having a sequence as set forth in SEQUENCE ID NO. 11, a PSI gene from barley having a sequence as set forth in SEQUENCE ID NO. 4, and an AFP gene from *Aspergillus giganteus* having a sequence as set forth in SEQUENCE ID NO. 1, and
   (b) a ChiS gene from *Serratia marcescens* having a sequence as set forth in SEQUENCE ID NO. 8, operably linked to a plant-functional promoter, wherein the plant is resistant to fungal attack.

2. A transgenic plant comprising
   (a) at least one gene operably linked to a plant-functional promoter, said gene being selected from the group consisting of a ChiG gene from barley having a sequence as set forth in SEQUENCE ID NO. 9, a GluG gene from barley having a sequence as set forth in SEQUENCE ID NO. 11, a PSI gene from barley having a sequence as set forth in SEQUENCE ID NO. 4, and a ChiS gene from *Serratia marcescens* having a sequence as set forth in SEQUENCE ID NO. 8, and
   (b) a AFP gene from *Aspergillus giganteus* having a sequence as set forth in SEQUENCE ID NO. 1, operably linked to a plant-functional promoter, wherein the plant is resistant to fungal attack.

3. A transgenic fungus-resistant plant according to claim 1 or 2 wherein the plant is a tobacco, potato, strawberry, corn, rape or tomato plant.

4. A purified and isolated DNA molecule comprising
   (a) at least one gene selected from the group consisting of a ChiG gene from barley having a sequence as set forth in SEQUENCE ID NO. 9, a GluG gene from barley having a sequence as set forth in SEQUENCE ID NO. 11, a PSI gene from barley having a sequence as set forth in SEQUENCE ID NO. 4, and an AFP gene from *Aspergillus giganteus* having a sequence as set forth in SEQUENCE ID NO. 1, and
   (b) a ChiS gene from *Serratia marcescens* having a sequence as set forth in SEQUENCE ID NO. 8.

5. A purified and isolated DNA molecule comprising
   (a) at least one gene selected from the group consisting of a ChiG gene from barley having a sequence as set forth in SEQUENCE ID NO. 9, a GluG gene from barley having a sequence as set forth in SEQUENCE ID NO. 11, a PSI gene from barley having a sequence as set forth in SEQUENCE ID NO. 4, and a ChiS gene from *Serratia marcescens* having a sequence as set forth in SEQUENCE ID NO. 8, and
   (b) an AFP gene from *Aspergillus giganteus* having a sequence as set forth in SEQUENCE ID NO. 1.

6. A process for the generation of a fungus-resistant plant according to claim 1 or 2, wherein a plant is transformed with at least one gene with fungus-inhibiting action, and the fungus-resistant plant is obtained by a method selected from the group consisting of
   (a) crossing the plant with another plant which contains at least one other gene, said gene having fungus-inhibiting action, and subsequently selecting the fungus-resistant plant, and
   (b) transforming the plant with at least one other gene, said gene having fungus-inhibiting action.

7. A process according to claim 6 which employs a DNA transfer vector comprising a gene selected from the group consisting of a ChiG gene from barley having a sequence as set forth in SEQUENCE ID NO. 9, a GluG gene from barley having a sequence as set forth in SEQUENCE ID NO. 11, a PSI gene from barley having a sequence as set forth in SEQUENCE ID NO. 4, an AFP gene from *Aspergillus giganteus* having a sequence as set forth in SEQUENCE ID NO. 1, and a ChiS gene from *Serratia marcescens* having a sequence as set forth in SEQUENCE ID NO. 8.

8. A process for the generation of a transgenic fungus-resistant plant comprising employing a DNA-vector comprising (a) at least one gene operably linked to a plant-functional promoter, said gene being selected from the group consisting of a ChiG gene from barley having a sequence as set forth in SEQUENCE ID NO. 9, a GluG gene from barley having a sequence as set forth in SEQUENCE ID NO. 11, a PSI gene from barley having a sequence as set forth in SEQUENCE ID NO. 4 and a ChiS gene from *Serratia marcescens* having a sequence as set forth in SEQUENCE ID NO. 8, and (b) an AFP gene from *Aspergillus giganteus* having a sequence as set forth in SEQUENCE ID NO. 1, operably linked to a plant-functional promoter, for transformation of a plant.

9. A process for the generation of transgenic fungus-resistant plant, comprising employing a DNA vector comprising (a) at least one gene operably linked to a plant-functional promoter, said gene being selected from the group consisting of a ChiG gene from barley having a sequence as set forth in SEQUENCE ID NO. 9, a GluG gene from barley having a sequence as set forth in SEQUENCE ID NO. 11, a PSI gene from barley having a sequence as set forth in SEQUENCE ID NO. 4 and an AFP gene from *Aspergillus giganteus* having a sequence as set forth in SEQUENCE ID NO. 1, and (b) a ChiS gene from *Serratia marcescens* having a sequence as set forth in SEQUENCE ID NO. 8, operably linked to a plant-functional promoter, for transformation of a plant.

\* \* \* \* \*

UNITED STATES PATENT AND TRADEMARK OFFICE
CERTIFICATE OF CORRECTION

PATENT NO. : 5,689,045

DATED : November 18, 1997

INVENTOR(S) : Jurgen Logemann et al.

It is certified that error appears in the above-identified patent and that said Letters Patent is hereby corrected as shown below:

Col. 1, line 14, "a" should read --by a-;

Col. 36, line 5, "of" should read --of a--.

Signed and Sealed this

Twenty-fifth Day of August, 1998

Attest:

BRUCE LEHMAN

Attesting Officer

Commissioner of Patents and Trademarks